United States Patent [19]

Hubele

[11] 4,151,295

[45] Apr. 24, 1979

[54] MICROBICIDES FOR CONTROLLING PLANT DISEASES

[75] Inventor: Adolf Hubele, Magden, Switzerland

[73] Assignee: Ciba-Geigy Corporation, Ardsley, N.Y.

[21] Appl. No.: 889,700

[22] Filed: Mar. 24, 1978

[30] Foreign Application Priority Data

Mar. 29, 1977 [CH] Switzerland .................. 3929/77

[51] Int. Cl.$^2$ .................... A01N 9/28; C07D 307/24; C07D 307/68

[52] U.S. Cl. ............................... 424/285; 260/347.3; 260/562 R; 260/562 A; 260/562 S; 424/324

[58] Field of Search ............ 260/347.3, 562 R, 562 S, 260/562 A; 424/285, 324

[56] References Cited

U.S. PATENT DOCUMENTS

| | | | |
|---|---|---|---|
| 3,590,083 | 6/1971 | Dexter et al. ............... | 260/562 S |
| 3,778,512 | 12/1973 | Krenzen et al. ............. | 424/285 |
| 3,878,248 | 4/1975 | Phillips ...................... | 260/562 S X |
| 3,959,481 | 5/1976 | Davis et al. ................. | 424/285 |
| 4,013,684 | 3/1977 | Merkle et al. .............. | 260/347.3 |
| 4,021,224 | 5/1977 | Pallos et al. ................ | 260/347.3 X |
| 4,088,687 | 5/1978 | Gaughan ..................... | 260/557 R |
| 4,094,990 | 6/1978 | Hubele ........................ | 424/285 |

OTHER PUBLICATIONS

Gaughan, Chemical Abstracts, vol. 82 (1975) 72769y.

*Primary Examiner*—Richard Raymond
*Attorney, Agent, or Firm*—Harry Falber

[57] ABSTRACT

Acylated sec-alkylanilines and acylated alkoxy-sec.alkylanilines of the formula I are valuable microbicides. They can be used in the form of compositions especially for controlling phytopathogenic fungi, such as Phytophthora, Plasmopara, Pythium, Puccinia, Cercospora, Erysiphe and others. The compounds have a systemic action.

20 Claims, No Drawings

MICROBICIDES FOR CONTROLLING PLANT DISEASES

The present invention relates to compounds of the formula

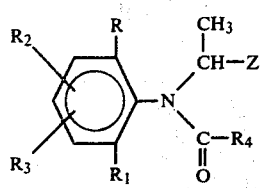

wherein

Z represents a methyl radical or an ethyl radical which can be interrupted by oxygen, or represents a propyl radical which can be interrupted by oxygen, R represents $C_1$-$C_4$alkyl, $C_1$-$C_4$alkoxy or halogen, $R_1$ represents $C_1$-$C_3$alkyl, $C_1$-$C_4$alkoxy or halogen, $R_2$ represents hydrogen, $C_1$-$C_3$alkyl, $C_1$-$C_4$alkoxy or halogen, $R_3$ represents hydrogen or methyl, with the proviso that the total number of carbon atoms of the substituents in the phenyl ring does not exceed 8, $R_4$ represents one of the following groups: a 2-furanyl or 2-tetrahydrofuranyl group which is unsubstituted or substituted by halogen, Y—O—$R_5$ or —$CH_2$—S—$R_5$, wherein Y represents —$CH_2$—, —$CH_2$—$CH_2$— or —$CH_2$—$CH(CH_3)$—, and $R_5$ represents $C_1$-$C_4$alkyl, $C_3$-$C_4$alkenyl or $C_3$-$C_4$alkynyl, to a process for the production of these compounds as well as to compositions which contain them as active ingredients, and to the use of these active ingredients as microbicides in plant protection.

By alkyl or as alkyl moiety of an alkoxy group are meant the following groups, depending on the stated number of carbon atoms: methyl, ethyl, propyl, isopropyl, butyl, isobutyl, secbutyl or tert-butyl. $C_1$-$C_3$alkenyl is to be understood as meaning allyl, methallyl or crotyl. $C_1$-$C_4$alkynyl is in particular propargyl and butynyl. The term "halogen" denotes fluorine, chlorine, bromine or iodine.

The substituent Z represents in particular the groups —$CH_3$, —$CH_2$—$CH_3$, —$CH_2$—O—$CH_3$ and —$CH_2$—O—$CH_2$—$CH_3$.

German Offenlegungsschrift No. 2,305,495 (=French Pat. No. 2,171,171) and German Offenlegungsschrift No. 2,328,340 (=French Pat. No. 2,187,225) describe herbicidal compounds which are similar in structure to the compounds of the formula I but contain a chloroacetyl group in place of the substituent $R_4$. Such compounds have almost no microbicidal action and on account of their pronounced herbicidal action are unsuitable for controlling plant diseases.

Surprisingly, it has now been found that compounds having the structure of the formula I possess for practical purposes a very advantageous microbicidal structure for protecting cultivated plants without adversely affecting them by undesirable side-effects. Examples of cultivated plants within the scope of the present invention are: cereals, maize, rice, vegetables, sugar-beet, soya, ground nuts, fruit trees, ornamentals, and in particular vines, hops, cucumber plants (cucumber, marrows, melons), solanaceae, such as potatoes, tobacco plants and tomatoes, and also banana, cocoa and natural rubber plants.

With the active compounds of the formula I it is possible to inhibit or destroy the fungi which occur in plants or parts of plants (fruit, blossoms, leaves, stems, tubers, roots) in these and also related crops of useful plants, and also to protect from attack by such fungi the parts of plants which grow later. The active compounds are effective against the phytopathogenic fungi which belong to the following classes: Ascomycetes (e.g. Erysiphaceae); Basidiomycetes, in particular rust fungi; fungi imperfecti (e.g. Moniliales e.g. (Cercospora); and especially against the Oomycetes belonging to the class of the Phycomycetes, such as Phytophthora, (Pseudo) Peronospora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

Preferred phytofungicides are anilides of the formula I, in which R represents methyl, ethyl, chlorine or bromine, $R_2$ represents hydrogen, halogen, para-$C_1$-$C_4$alkoxy or methyl and $R_3$ represents hydrogen or methyl, and Z, $R_4$ and $R_5$ are as defined in formula I. This group of compounds will be designated as Ia. Within this group of compounds Ia, those compounds are to be singled out for special mention in which $R_4$ represents methoxymethyl, ethoxymethyl, propoxymethyl, isopropoxymethyl, methoxyethyl, ethoxyethyl, 2-methoxypropyl, or an unsubstituted 2-furanyl or 2-tetrahydrofuranyl radical, and Z has the given meaning. This group of compounds will be designated Ib.

Interesting compounds within this group of compounds Ib are those in which Z represents —$CH_2$—O—$CH_3$ or —$CH_2$—O—$CH_2$—$CH_3$. This group of compounds will be designated Ic.

The compounds of the formula I are produced according to the invention by (A) acylation of a compound of the formula II

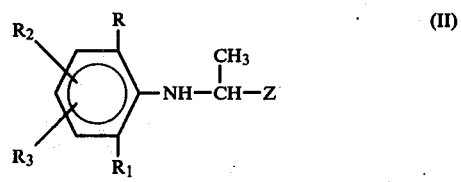

with a carboxylic acid of the formula III $$HO—CO—R_4 \qquad (III)$$

or the acid halide or acid anhydride thereof, or, if derivatives in which $R_4$ is Y—O$R_5$ or —$CH_2$—S—$R_5$ are desired, (B) by initial monohaloacetylation of a compound of the formula II to give a compound of the formula IV

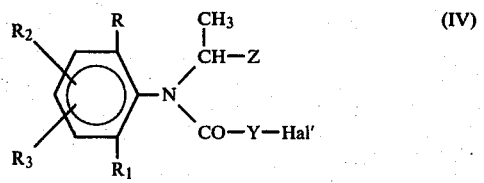

and further reaction with an alkanol M—O—R$_5$, or, if Y is —CH$_2$—, with a mercaptan M—S—R$_5$ or the metal salts thereof, preferably the alkali metal or alkaline earth metal salts thereof, or (C) by reaction of an already acylated aniline of the formula V

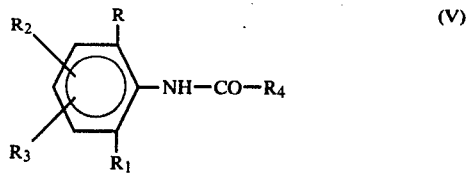

in the presence of a proton acceptor, such as butyl lithium or sodium hydride, with a compound of the formula VI

or (D) if it is desired to obtain β-aliphatoxyethyl compounds (R$_4$=Y—OR$_5$ and Y=—CH$_2$CH$_2$— or —CH$_2$—CH(CH$_3$)—), by Michael addition of an alcohol or the alkaline (or alkaline earth) alcoholate thereof MO—R$_5$ to an intermediate of the formula VII obtained by acylation with acrylic acid or crotonic acid, to give compounds of the formula I':

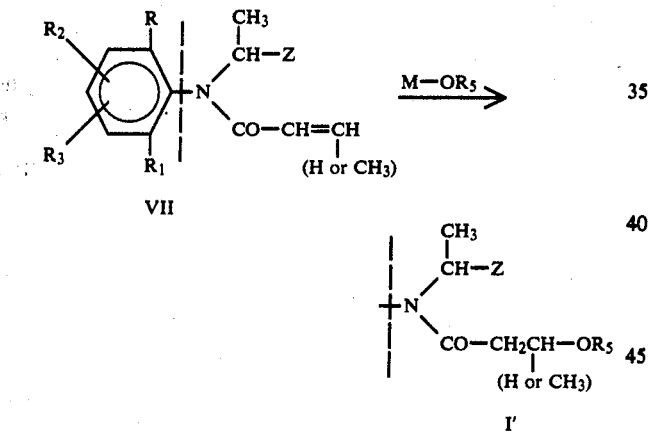

In the formulae II to VII and I', R to R$_5$ and Y are as defined in formula I, and Hal' and Hal" represent halogen, preferably chlorine or bromine, and M represents hydrogen or a metal cation (preferably alkali metal or alkaline earth metal).

This reaction may be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ether and ethereal compounds, such as dialkyl ethers, dioxane, tetrahydrofurane; nitriles, such as acetonitrile; N,N-dialkylated amides, such as dimethyl formamide, dimethyl sulphoxide, ketones, such as methylethylketone, and mixtures of such solvents. For the acylation of process A or C or for the monohaloacetylation of process B, it is possible to use the corresponding carboxylic acids themselves, but advantageously the acid anhydrides or acid halides, preferably the acid chlorides or acid bromides.

The reaction temperatures are between 0° and 180° C., preferably between 20° and 120° C. In many cases the use of acid acceptors or condensation agents is advantageous, for example tertiary amines, such as trialkylamines (e.g. triethylamine), pyridine and pyridine bases, or inorganic bases, such as the oxides and hydroxides, hydrogen carbonates and carbonates of alkali metals and alkaline earth metals, as well as sodium acetate.

Process A, starting from compounds of the formula II, as well as the acylating step resulting in compounds of the formula IV, can also be carried out without acid acceptors, whilst in some cases the introduction of nitrogen to expel hydrogen halide is expedient. In other cases it is very advantageous to add dimethyl formamide as reaction catalyst.

Intermediates of the formula II can be prepared by reaction of the aniline of the formula VIII

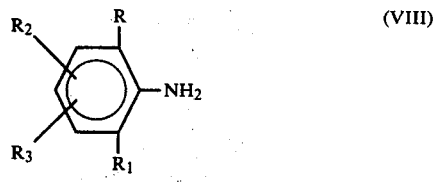

as defined in formula I, with a compound of the formula VI, wherein Z is as defined in formula I and Hal", in addition to representing halogen, can also represent another leaving group, for example the tosylate or brosylate. The reaction proceeds under the above described conditions.

The compounds of the formula I, or their primary products of the formulae II, IV or VI, possess a centre of asymmetry in the vicinal position to the group Z and can be separated into optical antipodes in conventional manner (e.g. fractional crystallisation or separation by chromatography). Both these configurations of the formula I have a differing pronounced microbicidal action. The influence of further possible centres of asymmetry in the molecule or the possible cis/trans-isomerism of an alkenyl substituent R$_5$ has no effect on the microbicidal activity of the entire molecule. Provided a synthesis with the object of isolating pure isomers of the formula I or their primary products is not carried out, a product will normally be obtained as an isomer mixture.

The following Examples will serve to illustrate the invention in more detail without imposing any restriction on it.

EXAMPLE 1

Preparation of 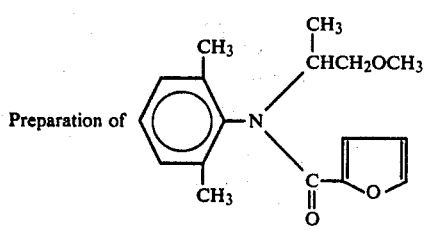

N-(1'-methyl-2'-methoxyethyl)-N-(furan(2")-carbonyl)-2,6-dimethylaniline.

With stirring, 19.2 g of furane-2-carboxylic acid chloride in 50 ml of abs. toluene were added at room temperature to 19.3 g of N-(1'-methyl-2'-methoxyethyl)-2,6- dimethylaniline in 100 ml of abs. toluene, whereupon the temperature rose from 20° to 38° C. After boiling for 2 hours under reflux and simultaneously introducing nitrogen, the reaction mixture was cooled to 30° C., washed with 200 ml of saturated sodium carbonate solution and with three 200 ml portions of water, dried over sodium sulphate, and filtered. The solvent was evaporated and the residual oil was crystallised by trituration with petroleum ether and recrystallised from hexane with the addition of activated carbon. Melting point: 74°–76° C.

The following compounds of the formula

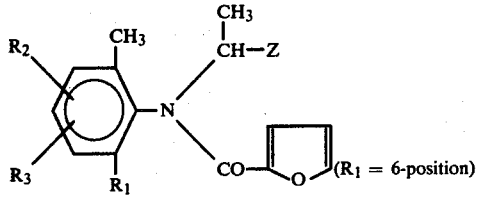

were prepared in analogous manner:

| Compound | $R_1$ | $R_2$ | $R_3$ | Z | Physical constant ° C. |
|---|---|---|---|---|---|
| 1.1 | $CH_3$ | H | H | $-CH_2OCH_3$ | mp. 74°–76° |
| 1.2 | $CH_3$ | 4-Br | H | $-CH_2OCH_3$ | mp. 71°–73° |
| 1.3 | $C_2H_5$ | H | H | $-CH_2OCH_3$ | mp. 43°–56° |
| 1.4 | $CH_3$ | 4-Cl | H | $-CH_2OCH_3$ | b.p.135°–137°/0.04 torr |
| 1.5 | $CH_3O$ | H | H | $-CH_2OCH_3$ | b.p.128°/0.03 torr |
| 1.6 | Cl | H | H | $-CH_2OCH_3$ | b.p.138°–140°/0.06 torr |
| 1.7 | $CH_3$ | 3-Br | H | $-CH_2OCH_3$ | oil |
| 1.8 | $C_2H_5$ | 4-Cl | H | $-CH_2OCH_3$ | oil |
| 1.9 | $CH_3$ | 3-$CH_3$ | H | $-CH_2OCH_3$ | mp. 47°–50° |
| 1.10 | $CH_3$ | 3-$CH_3$ | 5-$CH_3$ | $-CH_2OCH_3$ | mp. 67°–69° |
| 1.11 | $CH_3$ | H | H | $-CH_3$ | mp. 71°–72,5° |
| 1.12 | $CH_3$ | 4-Cl | H | $-CH_3$ | oil |
| 1.13 | $CH_3$ | H | H | $-C_2H_5$ | mp. 66°–67° |
| 1.14 | $CH_3$ | 4-Br | H | $-C_2H_5$ | oil |
| 1.15 | $C_2H_5$ | 4-Cl | H | $-C_2H_5$ | oil |
| 1.16 | $CH_3$ | H | H | $-CH_2OC_2H_5$ | mp. 78°–82° |
| 1.17 | $CH_3$ | 4-Cl | H | $-CH_2OC_2H_5$ | b.p.135°–138°/0.03 torr |
| 1.18 | $C_2H_5$ | 3-Br | H | $-CH_2OC_2H_5$ | oil |
| 1.19 | $CH_3$ | 3-$CH_3$ | H | $-CH_2OC_2H_5$ | mp.49°–52° |
| 1.20 | $CH_3$ | 3-$CH_3$ | 5-$CH_3$ | $-CH_2OC_2H_5$ | mp.67°–70° |
| 1.21 | Cl | H | H | $-CH_2OC_2H_5$ | b.p.130°–133°/0.04 torr | as well as the compounds of the formula

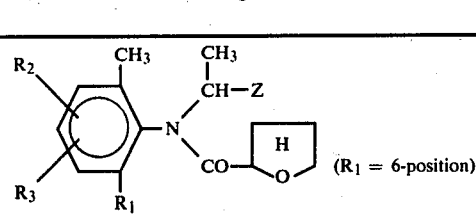

| Compound | $R_1$ | $R_2$ | $R_3$ | Z | Physical constant ° C. |
|---|---|---|---|---|---|
| 1.22 | $CH_3$ | H | H | $-CH_2OCH_3$ | oil |
| 1.23 | $CH_3$ | 3-$CH_3$ | H | $-CH_2OCH_3$ | oil |
| 1.24 | $CH_3$ | 3-$CH_3$ | 5-$CH_3$ | $-CH_2OCH_3$ | oil |
| 1.25 | Cl | H | H | $-CH_2OCH_3$ | mp.58°–65° |
| 1.26 | $C_2H_5$ | H | H | $-CH_2OCH_3$ | oil |
| 1.27 | $CH_3$ | 4-Cl | H | $-CH_2OCH_3$ | b.p.134°–135°/0.06 torr |
| 1.28 | $CH_3O$ | H | H | $-CH_2OCH_3$ | oil |
| 1.29 | $CH_3$ | 3-Br | H | $-CH_2OCH_3$ | oil |
| 1.30 | $CH_3$ | 4-sec.$C_4H_9O$ | H | $-CH_2OCH_3$ | oil |
| 1.31 | $CH_3$ | 4-$CH_3O$ | H | $-CH_2OCH_3$ | oil |
| 1.32 | $CH_3$ | H | H | $-CH_2OC_2H_5$ | oil |
| 1.33 | $CH_3$ | 3-$CH_3$ | H | $-CH_2OC_2H_5$ | oil |
| 1.34 | $CH_3$ | 3-Br | H | $-CH_2OC_2H_5$ | viscous |
| 1.35 | $CH_3$ | 4-Cl | H | $-CH_2OC_2H_5$ | b.p.135°/0.06 torr |
| 1.36 | Cl | 4-Br | H | $-CH_2OC_2H_5$ | viscous |
| 1.37 | $CH_3$ | H | H | $-CH_3$ | oil |
| 1.38 | $CH_3$ | 3-$CH_3$ | H | $-CH_2-CH_3$ | oil |
| 1.39 | Cl | H | H | $-CH_2-CH_3$ | b.p.85°–90°/0.06 torr |
| 1.40 | $CH_3$ | 4-Br | H | $-CH_2-CH_3$ | oil |

EXAMPLE 2

Preparation of

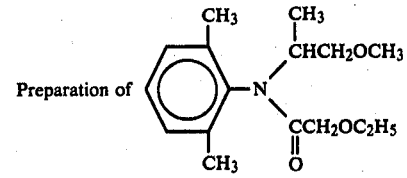

N-(1'-methyl-2'-methoxyethyl)-N-ethoxyacetyl-2,6-dimethylaniline.

With stirring, 7.3 g of ethoxyacetyl chloride in 20 ml of abs. toluene were added at room temperature to 9.6 g of N-(1'-methyl-2'-methoxyethyl)-2,6-dimethylaniline. After stirring for 3 hours at room temperature, the reaction mixture was filtered. The filtrate was freed from solvent and the residual oil was distilled in a high vacuum. Boiling point: 122°–124° C./0.04 torr.

The following compounds were prepared in analogous manner:

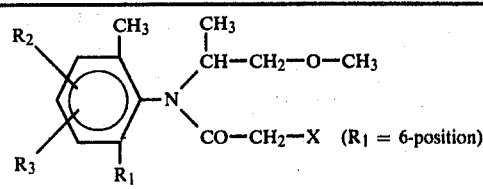

| Compound | $R_1$ | $R_2$ | $R_3$ | X | Physical constant ° C. |
|---|---|---|---|---|---|
| 2.1 | $CH_3$ | H | H | $-OCH_3$ | b.p.122°–124°/0.06 torr |
| 2.2 | $CH_3$ | H | H | $-OC_2H_5$ | b.p.122°–124°/ |

-continued

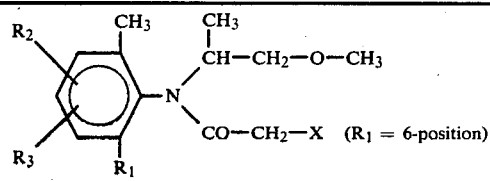

| Compound | $R_1$ | $R_2$ | $R_3$ | X | Physical constant °C. |
|---|---|---|---|---|---|
| 2.3 | $C_2H_5$ | H | H | $-OC_2H_5$ | b.p.125°/0.04 torr |
| 2.4 | $CH_3$ | 3-Br | H | $-OC_2H_5$ | b.p.118°/0.05 torr |
| 2.5 | $CH_3$ | 3-$CH_3$ | H | $-OC_2H_5$ | b.p.117°/0.01 torr |
| 2.6 | $CH_3$ | 3-$CH_3$ | 5-$CH_3$ | $-OC_2H_5$ | mp. 60°–61° |
| 2.7 | Cl | H | H | $-OCH_3$ | b.p.112°–114°/0.06 torr |
| 2.8 | $CH_3O$ | H | H | $-OisoC_3H_7$ | b.p.132°/0.08 torr |
| 2.9 | $CH_3$ | 4-Cl | H | $-OCH_3$ | b.p.132°/0.05 torr |
| 2.10 | $CH_3$ | 4-$isoC_3H_7O$ | H | $-OisoC_3H_7$ | b.p.168°/0.04 torr |
| 2.11 | $CH_3$ | 4-sec.$C_4H_9O$ | H | $-OCH_3$ | b.p.142°/0.01 torr |
| 2.12 | $CH_3$ | H | H | $-OnC_3H_7$ | b.p.128°/0.02 torr |
| 2.13 | $C_2H_5$ | H | H | $-OCH_3$ | b.p.130°–132°/0.04 torr |
| 2.14 | $C_2H_5$ | H | H | $-OC_2H_5$ | b.p.130°–132°/0.06 torr |
| 2.15 | $CH_3$ | 3-$CH_3$ | H | $-OCH_3$ | b.p.116°–118°/0.07 torr |
| 2.16 | Cl | H | H | $-OC_2H_5$ | b.p.120°–122°/0.04 torr |
| 2.17 | $CH_3$ | 3-$CH_3$ | 5-$CH_3$ | $-OCH_3$ | b.p.134°/0.08 torr |
| 2.18 | $CH_3$ | 4-Cl | H | $-OC_2H_5$ | b.p.121°–123°/0.04 torr |
| 2.19 | $isoC_3H_7$ | H | H | $-OCH_3$ | oil |
| 2.20 | $CH_3$ | H | H | $-CH_2OCH_3$ | b.p.136°–138°/0.05 torr |
| 2.21 | $C_2H_5$ | H | H | $-CH_2OCH_3$ | b.p.135°/0.02 torr |
| 2.22 | $CH_3$ | 3-$CH_3$ | H | $-CH_2OC_2H_5$ | b.p.127°/0.02 torr |
| 2.23 | $CH_3$ | 3-$CH_3$ | 5-$CH_3$ | $-CH_2OC_2H_5$ | b.p.135°–138°/0.04 torr |
| 2.24 | $CH_3$ | 3-$CH_3$ | H | $-CH_2OCH_3$ | b.p.117°/0.05 torr |
| 2.25 | $CH_3$ | 3-$CH_3$ | 5-$CH_3$ | $-CH_2OCH_3$ | b.p.133°–136°/0.04 torr |
| 2.26 | $CH_3$ | H | H | $-CH_2OC_2H_5$ | b.p.120°–122°/0.04 torr |
| 2.27 | Cl | H | H | $-CH_2OC_2H_5$ | b.p.128°–130°/0.1 torr |
| 2.28 | Cl | H | H | $-CH_2OCH_3$ | b.p.118°–120°/0.06 torr |
| 2.29 | $CH_3$ | H | H | $-CH(CH_3)OCH_3$ | oil |
| 2.30 | $CH_3$ | 3-$CH_3$ | H | $-CH(CH_3)OCH_3$ | b.p.118°–120°/0.06 torr |
| 2.31 | Cl | H | H | $-CH(CH_3)OCH_3$ | |
| 2.32 | $C_2H_5$ | H | H | $-CH(CH_3)OCH_3$ | oil |
| 2.33 | $isoC_3H_7$ | H | H | $-CH(CH_3)OCH_3$ | |
| 2.34 | $CH_3$ | H | H | $-CH(CH_3)OisoC_3H_7$ | oil |
| 2.35 | $CH_3$ | 4-$CH_3$ | H | $-CH_2OCH_3$ | |
| 2.36 | $CH_3$ | 4-$CH_3$ | H | $-CH_2OC_2H_5$ | oil | as well as the compounds 2.37 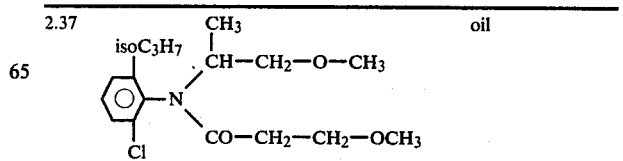 oil

-continued

| 2.38 | 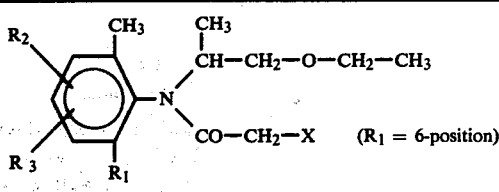 | b.p. 125°–127°/ 0.07 torr |
| --- | --- | --- |
| 2.39 | | viscous |

The following compounds were also prepared in analogous manner:

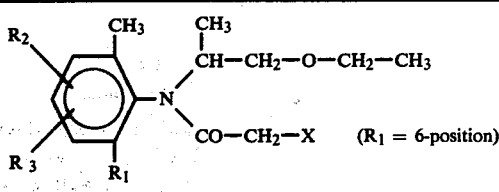

| Compound | $R_1$ | $R_2$ | $R_3$ | X | Physical constant °C. |
| --- | --- | --- | --- | --- | --- |
| 2.40 | $CH_3$ | H | H | $-OCH_3$ | oil |
| 2.41 | $CH_3$ | 3-$CH_3$ | H | $-OCH_3$ | |
| 2.42 | $C_2H_5$ | 3-$CH_3$ | H | $-OCH_3$ | |
| 2.43 | $CH_3$ | 4-$CH_3$ | H | $-OCH_3$ | |
| 2.44 | Cl | H | H | $-OCH_3$ | oil |

The following compounds were also prepared in analogous mannner:

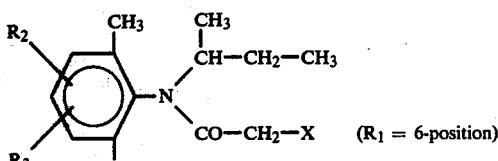

| Compound | $R_1$ | $R_2$ | $R_3$ | X | Physical constant °C. |
| --- | --- | --- | --- | --- | --- |
| 2.45 | $CH_3$ | H | H | $-OCH_3$ | b.p.92°/ 0.04 torr |
| 2.46 | $CH_3$ | H | H | $-OC_2H_5$ | b.p.111°/ 0.03 torr |
| 2.47 | $CH_3$ | H | H | $-isoC_3H_7$ | |
| 2.48 | Cl | H | H | $-OCH_3$ | |
| 2.49 | Cl | 4-Br | H | $-OCH_3$ | |
| 2.50 | $CH_3$ | 4-Cl | H | $-OCH_3$ | oil |
| 2.51 | $CH_3O$ | H | H | $-OCH_3$ | |
| 2.52 | $C_2H_5$ | H | H | $-OC_2H_5$ | |
| 2.53 | $CH_3$ | H | H | $-CH_2OCH_3$ | b.p.96°/ 0.02 torr |
| 2.54 | $CH_3$ | 3-$CH_3$ | H | $-CH_2OCH_3$ | |
| 2.55 | $CH_3$ | 3-$CH_3$ | 5-$CH_3$ | $-CH_2OCH_3$ | |
| 2.56 | Cl | H | H | $-CH_2OCH_3$ | oil |

EXAMPLE 3

Preparation of 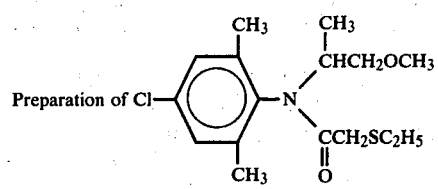

N-(1'-methyl-2'-methoxyethyl)-N-ethylthioacetyl-2,6-dimethyl-4-chloroaniline 2.5 g of ethylmercaptan were added to 9 g of 30% sodium methylate solution and after stirring for 1 hour at room temperature, 12.2 g of N-(1'-methyl-2'-methoxyethyl)-N-chloroacetyl-2,6-dimethyl-4-chloroaniline were added dropwise. After stirring for 1 day at room temperature, the reaction mixture was filtered to remove precipitated sodium chloride, the methanol was evaporated and the residual oil was distilled in a high vacuum. Boiling point: 130°–132° C./0.03 torr.

The following compounds were prepared in analogous manner or by one of the methods indicated above:

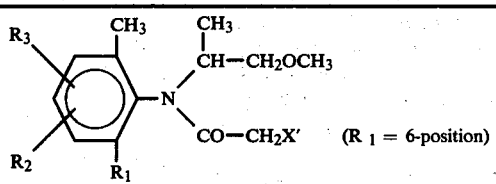

| Compound | $R_1$ | $R_2$ | $R_3$ | X' | Physical constant °C. |
| --- | --- | --- | --- | --- | --- |
| 3.1 | $CH_3$ | H | H | $-SCH_3$ | b.p.126°/ 0.03 torr |
| 3.2 | $CH_3$ | H | H | $-SC_2H_5$ | b.p.137°/ 0.03 torr |
| 3.3 | $CH_3$ | 4-Cl | H | $-SC_2H_5$ | b.p.130°–132°/ 0.03 torr |
| 3.4 | $C_2H_5$ | H | H | $-SCH_3$ | b.p.130°–132°/ 0.06 torr |
| 3.5 | $CH_3$ | 3-$CH_3$ | H | $-SCH_3$ | b.p.136°/ 0.04 torr |
| 3.6 | $CH_3$ | 3-$CH_3$ | H | $-SC_2H_5$ | b.p.149°–152° 0.02 torr |
| 3.7 | $CH_3$ | 3-$CH_3$ | 5-$CH_3$ | $-SCH_3$ | oil |
| 3.8 | $CH_3$ | 4-Cl | H | $-SCH_3$ | b.p.136°/ 0.02 torr |

The compounds of the formula I can be used by themselves or together with suitable carriers and/or other additives. Suitable carriers and additives can be solid or liquid and correspond to the substances normally used in the art of formulation, for example natural or regenerated mineral substances, solvents, dispersants, wetting agents, tackifiers, thickeners, binders or fertilisers.

The content of active substance in commercial compositions is between 0.1 and 90%.

For application the compounds of the formula I may be processed to the following formulations (in which the parts by weight refer to advantageous amounts of active substance):

Solid formulations: dusts, tracking agents (up to 10%), granules (coated granules, impregnated granules and homogeneous granules); pellets (1 to 80%);

Liquid formulations:

(a) active substance concentrates which are dispersible in water: wettable powders, pastes (25-90% in commercial packs, 0.01 to 15% in ready-for-use solutions); concentrated emulsions and solutions (10 to 50%; 0.01 to 15% in ready-for-use solutions).

(b) Solutions (0.1 to 20%); aerosols. The active substances of the formula I of the present invention can be formulated for example as follows:

Dusts: The following substances are used to prepare (a) 5% and (b) a 2% dust:

(a) 5 parts of active substance 95 parts of talc;

(b) 2 parts of active substance 1 part of highly dispersed silicic acid 97 parts of talc.

The active substances are mixed with the carriers and ground and in this form can be processed to dusts for application.

Granulate: The following substances are used to prepare a 5% granulate:

5 parts of active substances
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combating soil fungi.

Wettable powders: The following constituents are used to prepare (a) a 70%, (b) a 40%, (c) and (d) a 25% and (e) a 10% wettable powder:

(a)
70 parts of active substance,
5 parts of sodium dibutylnaphthylsulphonate
3 parts of naphthalenesulphonic acid/phenolsulphonic acid/formaldehyde condensate (3:2:1)
10 parts of kaolin
12 parts of Champagne chalk.

(b)
40 parts of active substance
5 parts of sodium ligninsulphonate
1 part of sodium dibutylnaphthalenesulphonic acid
54 parts of silicic acid.

(c)
25 parts of active substance
4.5 parts of calcium ligninsulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin.

(e)
10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

Emulsifiable concentrates: The following substances are used to prepare a 25% emulsifiable concentrate:

25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

EXAMPLE 4

Action against Cercospora personata (=C. arachidicola) on ground nut plants

Three-week-old ground nut plants were sprayed with a spray mixture (containing 0.02% of active substance) prepared from a wettable powder of the active substance. After about 12 hours the treated plants were infected by dusting with a conidia suspension of the fungus. The infected plants were then incubated for approx. 24 hours at >90% relative humidity and then stood in a greenhouse at approx. 22° C. The fungus attack was evaluated after 12 days.

In comparison to the untreated control, plants treated with active substances of the formula I exhibited a slight or almost no attack by fungus. The attack by fungus was completely inhibited by compounds 1.4, 1.9, 1.13, 2.27, 3.3 and others.

EXAMPLE 5

Action against Phytophthora infestans on tomatoes (a) Curative Action

"Roter Gnom" tomato plants were sprayed when 3 weeks old with a zoospore suspension of the fungus and incubated in a climatic chamber at 18° to 20° C. and saturated humidity. The humidifying was interrupted after 24 hours. After the plants had dried, they were sprayed with a spray mixture containing the active substance formulated as a wettable powder in a concentration of 0.06%. After the spray coating had dried, the plants were again kept in the humid chamber for 4 days. The effectiveness of the tested substances was assessed by determining the size and number of the typical leaf specks which had occured during this time.

(b) Preventive-systemic action

The active substance formulated as a wettable powder was applied in a concentration of 0.006% (referred to the volume of the soil) to the surface of the soil of 3-week old "Roter Gnom" tomatoes in pots. Three days later the underside of the leaves of the plants was sprayed with zoospore suspension of Phytophthora infestans. The plants were then kept in a spray chamber at 18° to 20° C. and saturated humidity for 5 days, after which time typical leaf specks formed. The effectiveness of the tested substance was assessed by determining the size and number of the specks. In both the above partial tests, the compounds of the formula I exhibited a good leaf-fungicidal action.

(I) Curative action: Complete or almost complete inhibition of fungus attack (0-5% attack) was effected with compounds 1.1, 1.9, 1.23, 1.24, 1.25, 2.2, 2.9, 2.13, 2.14, 2.17, 2.18 and 3.7. These effects were also obtained with the following compounds in a concentration of 0.02%: 1.1, 1.9, 1.23, 2.14, 2.17 and 3.7.

(II) Preventive systemic action: Complete or almost complete inhibition of fungus attack (0-5% attack) was effected with compounds 1.1, 1.4, 1.6, 1.10, 1.22, 1.24, 1.26, 2.1, 2.2, 2.5, 2.6, 2.7, 2.9, 2.13, 2.14, 2.15, 2.16, 2.18, 2.20, 2.21, 2.22, 2.23, 2.25, 2.26, 2.30, 2.45, 3.1, 3.5, 3.6. This effect was also obtained with the following compounds in an active substance concentration of 0.002%: 1.1, 1.10, 2.1, 2.2, 2.6, 2.7, 2.13, 2.14, 2.18, 2.30, 2.45, 3.1.

The following effects were obtained with the compound, 2,6-dimethyl-N-(1-methyl-2-methoxyethyl)-chloroacetanilide, known from German Offenlegungsschrift No. 2,305,495:

(I) (0.06%): 20-40% fungus attack
(II) (0.006%): 20-40% fungus attack.

The following effects were obtained with the compound, 2-ethyl-6-methyl-N-(1-methyl-2-methoxyethyl)-chloroacetanilide, known from German Offenlegungsschrift No. 2,328,340:

(I) (0.06%): 20-40% fungus attack
(II) (0.006%): 20-40% fungus attack.

The attack of untreated but infected control plants was used in each case as standard (=100% fungus attack).

EXAMPLE 6

Action on Plasmopara viticola (Bert. et Curt.) (Berl. et de Toni) on vines (a) Residual preventive action Vine cuttings of the variety "Chasselas" were reared in a greenhouse. Three plants in the 10-leaf stage were sprayed with a spray mixture (containing 0.06% of active substance) prepared from the active substance and formulated as a wettable powder. After the coating layer had dried, the plants were infected on the underside of the leaves with the spore suspension of the fungus. The plants were subsequently kept in a humid chamber for 8 days, after which time symptoms of the disease were visible on the control plants. The effectiveness of the tested substances was assessed by determining the number and size of the infected areas on the treated plants. A pronounced fungicidal action was obtained with the compounds of the formula I, especially those of the group I*b*. Compounds 1.9, 2.2, 2.7, 2.15, 2.24, 3.5 and others inhibited the fungus attack completely or almost completely (0-5% attack).

EXAMPLE 7

Action on Pythium debaryanum on sugar beets (a) Action after soil application

The fungus is cultivated on sterile oat grains and added to a mixture of earth and sand. Flower pots are filled with the infected soil in which sugar beet seeds are then sown. Immediately after sowing, the test preparations formulated as wettable powders are poured in the form of aqueous suspensions over the soil (20 ppm of active substance, referred to the volume of the soil). The pots are then stood for 2-3 weeks in a greenhouse at 20°-24° C. The soil is kept uniformly moist by gently spraying it with water.

(b) Action after seed dressing application

The fungus is cultivated on sterile oat grains and added to a mixture of earth and sand. Flower pots are filled with the infected soil and sugar beet seeds which have been treated with the test preparations formulated as seed dressing powders are sown therein (100 ppm of active substance, referred to the weight of the seeds). The pots are then stood in a greenhouse for 2-3 weeks at 20°-24° C. The soil is kept uniformly moist by gently spraying it with water. The emergence of the sugar beet plants as well as the number of healthy and sick plants are ascertained in evaluating the tests. Compounds of the formula I exhibited a pronounced action in that as a rule about 80% of the plants emerged in a healthy state. More than 85% of the plants emerged when treated with one of the compounds 1.1, 1.9, 1.13, 1.22, 1.23, 1.24, 1.25, 2.5, 2.6, 2.9, 2.13, 2.16, 2.17, 2.20, 2.22, 2.24, 2.45, 2.46, 3.2, 3.6, 3.7. More than 90% of the plants emerged when treated with one of the compounds 2.1, 2.2, 2.7, 2.15, 3.1 and 3.5.

EXAMPLE 8

Action against Puccinia triticina on wheat

Systemic action

A spray mixture (0.01% of active substance, based on the volume of the soil) prepared from the active substance formulated as wettable powder was applied to wheat plants 5 days after sowing. The treated plants were infected 48 hours later with a uredospore suspension of the fungus. After incubation for 48 hours at 95-100% relative humidity and about 20° C., the infected plants were stood in a greenhouse at about 22° C. Evaluation of rust development was made 12 days after infection. A number of the compounds of the formula I exhibited pronounced action, for example 1.6, 1.9, 2.5, 2.7, 2.16, 2.25, 2.27, 2.30.

EXAMPLE 9

Action on Erysiphe graminis on barley (Hordeum vulgare)

Residual protective action

Barley plants approx. 8 cm in height were sprayed with a spray mixture (0.06% of active substance) prepared from a wettable powder of the active substance. After 48 hours the treated plants were dusted with conidia of the fungus. The infected barley plants were stood in a greenhouse at approx. 22° C. and the fungus infection was evaluated after 10 days.

In general the compounds of the formula I exhibited a pronounced action against barley mildew. The attack of the fungus was completely inhibited by treatment with one of the compounds Nos. 1.22, 1.25, 1.26, 2.27, 2.28, 2.53 and 3.8.

What is claimed is:

1. A compound of the formula

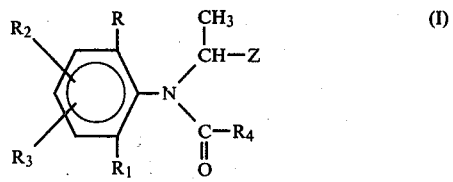

wherein
Z represents a methyl radical or an ethyl radical which can be interrupted by oxygen, or represents a propyl radical which can be interrupted by oxygen, R represents $C_1$-$C_4$alkyl, $C_1$-$C_4$alkoxy or halogen, $R_1$ represents $C_1$-$C_3$alkyl, $C_1$-$C_4$alkoxy or halogen, $R_2$ represents hydrogen, $C_1$-$C_3$alkyl, $C_1$-$C_4$alkoxy or halogen, $R_3$ represents hydrogen or methyl, with the proviso that the total number of carbon atoms of the substituents in the phenyl ring does not exceed 8, $R_4$ represents one of the following groups: a 2-furanyl or 2-tetrahydrofuranyl group which is unsubstituted or substituted by halogen, Y—O—$R_5$ or —$CH_2$—S—$R_5$, wherein Y represents —$CH_2$—, —$CH_2$—$CH_2$— or —$CH_2$—$CH(CH_3)$—, and $R_5$ represents $C_1$-$C_4$alkyl, $C_3$-$C_4$alkenyl or $C_3$-$C_4$alkynyl.

2. Compounds according to claim 1, wherein R represents methyl, $R_1$ represents methyl, ethyl, chlorine or bromine, and $R_2$ represents hydrogen, halogen, p-$C_1$-$C_4$ alkoxy or methyl.

3. Compounds according to claim 2, wherein $R_4$ represents methoxymethyl, ethoxymethyl, propoxymethyl, isopropoxymethyl, methoxyethyl, ethoxyethyl, 2-methoxypropyl, or an unsubstituted 2-furanyl or 2-tetrahydrofuranyl radical.

4. Compounds according to claim 3, wherein Z represents one of the radicals —$CH_2$—O—$CH_3$ or —$CH_2$—O—$CH_2CH_3$.

5. N-(1'-methyl-2'-methoxyethyl)-N-methoxyacetyl-2,6-dimethylaniline according to claim 1.

6. N-(1'-methyl-2'-methoxyethyl)-N-ethoxyacetyl-2,6-dimethylaniline according to claim 1.

7. N-(1'-methyl-2'-methoxyethyl)-N-(furan(2'')-carbonyl)-2,6-dimethylaniline according to claim 1.

8. N-(1'-methyl-2'-methoxyethyl)-N-methoxyacetyl-2,3,6-trimethylaniline according to claim 1.

9. N-(1'-methyl-2'-methoxyethyl)-N-methoxyacetyl-2-methyl-6-chloroaniline according to claim 1.

10. A microbicidal composition which contains as active ingredient a microbicidally effective amount of a compound of claim 1 together with suitable carriers and/or surface active agents.

11. A microbicidal composition which contains as active ingredient a microbicidally effective amount of a compound as claimed in claim 2, together with a suitable carrier.

12. A microbicidal composition which contains as active ingredient a microbicidally effective amount of a compound as claimed in claim 3, together with a suitable carrier.

13. A microbicidal composition which contains as active ingredient a microbicidally effective amount of a compound as claimed in claim 4, together with a suitable carrier.

14. A microbicidal composition which contains as active ingredient a microbicidally effective amount of a compound as claimed in claim 5, together with a suitable carrier.

15. A microbicidal composition which contains as active ingredient a microbicidally effective amount of a compound as claimed in claim 6, together with a suitable carrier.

16. A microbicidal composition which contains as active ingredient a microbicidally effective amount of a compound as claimed in claim 7, together with a suitable carrier.

17. A microbicidal composition which contains as active ingredient a microbicidally effective amount of a compound as claimed in claim 8, together with a suitable carrier.

18. A microbicidal composition which contains as active ingredient a microbicidally effective amount of a compound as claimed in claim 9, together with a suitable carrier.

19. A method of controlling phytopathogenic fungi and preventing attack by fungus, which comprises treating plants, parts of plants or their environment with a fungicidally effective amount of a compound of claim 1.

20. A method as claimed in claim 19, wherein in said compound R represents methyl, $R_1$ represents methyl, ethyl, chlorine or bromine, and $R_2$ represents hydrogen, halogen, p-$C_1$-$C_4$ alkoxy or methyl.

* * * * *